(12) United States Patent
Peccora et al.

(10) Patent No.: US 7,721,946 B2
(45) Date of Patent: May 25, 2010

(54) SENIOR CITIZEN COMMUNICATION SYSTEM

(76) Inventors: Orlando Peccora, 2710 Thompson Crossing, Richmond, TX (US) 77469; Donald W. Sapaugh, 227 E. Edgewood Ave., Friendswood, TX (US) 77546

( * ) Notice: Subject to any disclaimer, the term of this patent is extended or adjusted under 35 U.S.C. 154(b) by 598 days.

(21) Appl. No.: 11/708,744

(22) Filed: Feb. 21, 2007

(65) Prior Publication Data

US 2008/0201422 A1 Aug. 21, 2008

(51) Int. Cl.
*G06K 5/00* (2006.01)
*G06K 15/00* (2006.01)
*G06F 17/00* (2006.01)

(52) U.S. Cl. .................. 235/375; 235/383; 235/380

(58) Field of Classification Search .......... 235/375, 235/380, 383, 385, 486, 487, 492
See application file for complete search history.

(56) References Cited

U.S. PATENT DOCUMENTS

| | | | | |
|---|---|---|---|---|
| 6,012,035 A * | 1/2000 | Freeman et al. | ............... | 705/2 |
| 6,421,650 B1 * | 7/2002 | Goetz et al. | ................... | 705/3 |
| 6,994,249 B2 * | 2/2006 | Peterka et al. | ............... | 235/375 |
| 7,558,380 B2 * | 7/2009 | DiVenuta et al. | .......... | 379/88.18 |
| 2003/0195670 A1 * | 10/2003 | Smith et al. | .................... | 701/1 |
| 2004/0172290 A1 * | 9/2004 | Leven | ........................... | 705/2 |
| 2006/0007314 A1 * | 1/2006 | Fong | ..................... | 348/207.99 |
| 2006/0075052 A1 * | 4/2006 | Oostendorp | ................. | 709/206 |
| 2006/0105301 A1 * | 5/2006 | Chriss | ........................ | 434/112 |
| 2007/0047533 A1 * | 3/2007 | Criddle et al. | .............. | 370/356 |
| 2008/0261569 A1 * | 10/2008 | Britt et al. | ................ | 455/414.1 |

* cited by examiner

*Primary Examiner*—Thien M Le
(74) *Attorney, Agent, or Firm*—Richard L. Moseley

(57) ABSTRACT

A system and method is disclosed whereby a patient at a senior care facility can send and receive messages via the inter-net. Tools are provided to manage the patients, the patient's relative contact, mail and photo collection. Relatives can be designated to suggest changes to the contacts and edit the contents of the patient's contacts files. The messages may be audio, video or text and the user friendly system helps the patients navigate through the process. Notification is provided so that the relatives and patients know when a message had been received. Further notification is provided if a prolonged period lapses after receipt of a message to a patient and the message has not been read.

9 Claims, No Drawings

SENIOR CITIZEN COMMUNICATION SYSTEM

BACKGROUND OF THE INVENTION

1. Field of the Invention

The present invention relates to a system and method that allows senior citizens to communicate effectively with relatives and friends over long distances. More particularly the invention relates to a combination hardware-software-internet system that is simple to use by senior citizens and may allow communications of messages, photographs and video clips.

2. Related Art

The present state of the internet allows knowledgeable persons to communicate effectively over long distances. With the proper equipment, software and subscription to an internet provider people may now transmit messages and a wide variety of audio and video images. However, even the most basic systems, such as the Microsoft® television based system, require the use of the computer keyboard. Such systems are often confusing to elderly senior citizens many of whom have never been confronted with a computer before.

SUMMARY OF THE INVENTION

The present invention provides a simple and friendly application which allows senior citizen patients in care facilities to communicate effectively with their relatives. The system allows control of the relatives and friends who may contact the patient.

The system is set up by an administrator who can add, delete and edit patients, relatives and other operators. Each of the patients, relatives and other operators are assigned a user name and password which is stored on the web site in the host computer. In addition each is identified at least by a email address to which messages can be referred. The relatives are associated with a particular patient and one of the relative is designated the LEGAL GUARDIAN who may contact the administrator with suggestions to control the access to an individual patient. Both the patient and the relative must log onto the web page with the user name and password before any contact is established. Basically the messages are stored on the web page under the relative's or patient's file. The relative is notified of a message from a patient when he logs on. The patient is notified of any new messages by the administrator who reviews a list of all new messages when he logs on. Generally a written notification will be given the patient who may then log on and view the message at his leisure. The system notifies the administrator and/or designated relative(s) when a message to a patient has not been accessed after a predetermined time period, e.g., two to three days.

The key to the host computer is that it must be very user friendly. For that reason all menus are displayed prominently on the patient's computer and are accessed by standard touch screen technology. There are a limited number of choices on each menu and sub menu and they are all self explanatory. Relatives are expected to have a higher level of computer literacy than the patients and the menu choices may be made by the use of a mouse or the arrow keys on the relative's computer.

DETAILED DESCRIPTION OF THE PREFERRED EMBODIMENT

The following terms have the meaning indicated herein:

Patient: senior adults living at a facility who have access to the host computer through terminals placed at the facility.

Relative: relatives or friends of seniors who can receive messages from a patient or send messages to a patient. The users have access to the web page of the system through a conventional web browser. In order tp sen/receive messages from/to patients these users have to be linked to them by the relative network (see below).

Facility: a place proving lodging and/or care for senior adult patients.

Facility operator: an employee with special access to the system to administer the patient, relative and care takers in a specific facility. This person may also be referred to as the administrator.

Facility director: the person in charge of the facility.

Administrator/Operator: a user with total access (see facility operator).

Relative network: The list of relatives and friends related to a specific patient. A "Relative" user of the system has to be linked to a specific "Patient" in order to send messages and receive messages from him. The relative network is seen by the patient as his "Address Book".

Contact List: same as relative network.

Address Book: same as relative network for an individual patient.

Message: a piece of date sent by a user of the system to another user of the system. This date can be plain text, audio, video (moving pictures and audio) or photographs.

Message notification tool: a special alone application which is installed in the relative's tray bar and notifies his about new messages as soon as they get in his in box.

Pictures/Photo album: a collection of pictures linked to a specific patient and that are shown in a photo album-like way.

Alert message: a special notification message sent to the operator/care takers/relatives by the system to notify them that a patient has not read a message for a specific period of time.

The method comprises providing a host computer for a web page which can be accessed by a standard web browser used by the relatives. The web page/site can also be accessed by computer terminals within the facility. The web page/site is configured to receive information about each of the patients, their relatives and friends, receive and transmit messages between patients and relatives and provide the basic administration of the system. In addition the computer terminals include software and hardware for creating text, video and audio data messages which can be uploaded onto the web page/site for viewing by relatives.

The administrator/operator begins the method by installing the software which includes a special log on procedure to identify the administrator. The administrator controls the system by managing access (adding, editing or deleting patients, relatives and operators), and managing the messages sent and received by the patients. This is achieved by the administrator logging onto the system and selecting the MANAGE USERS option from the menu whereupon the following options appear on the screen:

Manage Patients
Manage Relative Network
Manage Operators
New Message Notification Each sub option above has a sub option to add, edit or delete.

To add a patient, the operator selects that option and enters the patient's first name, last name, user name, password, birth date, gender, email, room number, location and home town code. To add a relative, the administrator enters the patient's last name or user name and selects "ADD RELATIVE" at the prompt whereupon the administrator enters the relative's first name, last name, user name, password, birth date, gender, email, location and home town code. To add an operator the administrator selects the ADD OPERATOR option and enters the operator's first name, last name, user name, password, birth date, email, location and facility code. After entering the date the administrator selects ACCEPT from the prompt. Adding relatives creates the RELATIVE NETWORK and the patient's ADDRESS BOOK. When adding a relative, one of the relatives can be designated the LEGAL GUARDIAN who can send messages to the administrator, by-passing the patient.

To edit, the administrator selects the EDIT option from the menu (he is already in one of the Patient, etc sub menus) and enters the patient's, relative's or operators first name, last name or user name at the prompt. Then the administrator must reenter all of the information describing the user (see above) before the system prompts the administrator to edit the data. Editing relatives edits the RELATIVE NETWORK and the patient's ADDRESS BOOK.

To delete, the administrator selects the DELETE option from the menu (he is already in one of the Patient, etc sub menus) and enters the patient's, relative's or operators first name, last name or user name at the prompt. Then the administrator must reenter all of the information describing the user (see above) before the system prompts the administrator to DELETE the data. The only special case is that an operator/administrator cannot delete himself, i.e. the system will not allow the administrator who is logged on the system to delete himself. Deleting a relative deletes that relative from the RELATIVE NETWORK and the patient's ADDRESS BOOK.

Relative Messages

When a relative accesses the web page via his web browser the system prompts him to enter his user name and password. Immediately upon logging onto presents him with the menu option MANAGE MESSAGES. If he chooses this option (using his mouse or arrow keys and <enter>) the following menu appears:

RECEIVED MESSAGES
SENT MESSAGES
DELETED MESSAGES
CREATE MESSAGE.

If he selects RECEIVED MESSAGES the system shows the list of the user's received messages and the menu options;

Create New Message
Delete Message
Mark as read
Mark as not read.

The relative may then select a message by highlighting it with the mouse or arrow keys and pressing <enter> and a VIEW MESSAGE PROMPT appears and the relative again presses <enter>. If the message is a video message a movie screen appears with a play button appears with a prompt to select the play button which plays the movie. If the message is audio the system simply shows a play button with a prompt to select the play button which plays the message. If the message is text the message is displayed. In all case at the end of the messages the prompts REPLY or FORWARD are displayed. If either are selected the relative create message (below) is activated. In the case of the text message and additional prompt PRINT MESSAGE appears which allows the relative to print the message. If he has highlighted a message he may select one of the options. If he selects "Create New Message" the relative create message (below) is activated. If he selects "Delete Message" the system moves the message to his trash folder. If he selects "Mark as read" the system turns the message state to "read". Conversely if he selects "Mark as unread" the system turns the message state to "not read".

If he selects SENT MESSAGES the system shows a list of of the user's sent message and the options "Create New Message" and "Delete Message". He may select any message by highlighting it using his mouse or arrow keys and perform either of the option on the highlighted message which will activate the relative create message (below) or send the message to his trash folder.

If he selects DELETED MESSAGES the system shows a list of the user's trashed messages and the options "Create New Message" and "Delete permanently". If the relative selects create new message the relative create message will (below) will be activated. If he highlights a message using his mouse or arrow keys and selects that message the VIEW MESSAGE (above) prompt appears. If he highlights a message and selects "delete permanently" the system will delete the message from the user's mailbox.

If the relative selects the CREATE MESSAGE option from the main menu the system shows the sub menu:

Create Voice Message
Create Video Message
Create Text Message.

If the relative selects "create video message" the system prompts the relative to enter the linked patient's email address and the subject. After the relative enters the information the system prompts the relative to select the "play" button (using his mouse) to start recording the video message after which the relative presses "play" and records his message. The messages lengths are set at a predetermined time and a count down is shown at the bottom of the screen. When the relative finishes the message he presses "stop" (using his mouse) or the system automatically stops recording. A "preview" button allows the relative to view the message. A "discard" button allows the relative to have the system delete the message. The system also has a "send" button which the relative actuates to have the system upload the recorded message to the patient's in box.

If the relative selects "create voice message" the system prompts the relative to enter the linked patient's email address and the subject. After the relative enters the information the system prompts the relative to select the "play" button (using his mouse) to start recording the video message after which the relative presses "play" and records his message. The messages lengths are set at a predetermined time and a count down is shown at the bottom of the screen. When the relative finishes the message he presses "stop" (using his mouse) or the system automatically stops recording. A "preview" button allows the relative to view the message. A "discard" button allows the relative to have the system delete the message. The system also has a "send" button which the relative actuates to have the system upload the recorded message to the patient's in box.

If the relative selects "create text message" the system prompts the relative to enter the linked patient's email address and the subject and the text message. After the information has been entered the system prompts the relative to press the "send" button which uploads the message to the patients in box.

In any of the cases if the upload should fail the system shows an alert notifying that the connection has some problems and asks that the relative try again in a moment and asks for confirmation from the relative.

Patient Messages

The patient viewing process begins by the administrator logging onto the system and selecting the menu option NEW MESSAGE NOTIFICATION. The system displays a list with the name of II the patients who have one or more new messages. When the administrator selects a patient then options "Print Notification" or "Delete Notification" appears If "Print Notification" is selected a printed message reading Dear [patient name]

You have received a [video/voice/text] message from [Relative Name] on [date and time]. Please visit the Senior In Touch computer to see your message Thank you, and have a pleasant day.

After printing the notification the system marks the notification as read. If the administrator chooses "Delete Notification" the system deletes it.

When the patient has been notified that he has a new message (see below) or wishes to communicate with someone in his relative network he logs onto the system by entering his user name and password. This may be done for him by a care giver at the facility. The main menu is displayed on a touch screen with the following options:

VIEW NEW MESSAGES
VIEW SAVED MESSAGES
PHOTO ALBUM
CREATE NEW MESSAGE.

If the patient selects VIEW NEW MESSAGES or VIEW OLD MESSAGES by touching the screen, the system displays a list of the messages which includes the date, subject, sender and message type, i.e., video, audio or text. The patient then selects a message from the list by touching the message on the screen and if the message is a video message a movie screen appears along with the buttons "Play", "Save Message", "Delete Message" and reply, and the systems prompts the patient to select the "Play" button to see the movie. If the patient presses "Save Message" the system saves the message. If the patient presses the "Delete Message" the system deletes the message. If the patient presses "Reply" the "patient create message" (see below) is actuated. If the message is a voice message the system shows the message date, subject and the buttons "Play", "Save Message", Delete Message" and "Reply". To hear the message the patient presses play. If the patient presses "Save Message" the system saves the message. If the patient presses the "Delete Message" the system deletes the message. If the patient presses "Reply" the "patient create message" (see below) is actuated. If the message is a text message the system shows the message date, subject, body and the buttons "Play", "Save Message", Delete Message" and "Reply". If the patient presses "Save Message" the system saves the message. If the patient presses the "Delete Message" the system deletes the message. If the patient presses "Reply" the "patient create message" (see below) is actuated. If in any case the message fails the system shows an alert notifying that the connection has some problems and asks that the relative try again in a moment and asks for confirmation from the patient.

If the patient selects CREATE NEW MESSAGE the system shows the sub menu:

Create New Text Message
Create New Voice Message
Create New Video Message.

If the patient selects "Create New Video Message" the system shows a video movie screen with the buttons "Stop Recording", "Preview Video", "Discard Messge" and "Send Message". The system begins recording automatically through its camera after a predetermined time period, e.g., fifteen seconds, and prompts the patient to press the "Stop" button when the patient finishes the message. The message is automatically saved into a temporary file. The maximum length of the recording is also predetermined, i.e., two minutes, and automatically stops recording if that time period is reached. After the patient stops the recording he may: (1) preview the message by pressing the "Preview Video" button; (2) discard the message by pressing the "Delete Message" button whereupon the system deletes the saved message; or (3) send the message by pressing the "Send" button. When the "Send" button is pressed the system displays a list with the patients contact—the relative network or address book—and the system prompts the patient to select the contacts which will receive the message. The patient selects one or more of the contacts and the system prompts the patient to press "Send". When the patient presses "Send" the system automatically sends the message to the inbox of the selected contacts in the system.

If the patient selects "Create New Voice Message" the system simply shows the buttons "Stop Recording", "Preview Audio, "Discard Message", and "Send Message". The system begins recording automatically through its microphone after a predetermined time period, e.g., fifteen seconds, and prompts the patient to press the "Stop" button when the patient finishes the message. The message is automatically saved into a temporary file. The maximum length of the recording is also predetermined, i.e., two minutes, and automatically stops recording if that time period is reached. After the patient stops the recording he may: (1) preview the message by pressing the "Preview Video" button; (2) discard the message by pressing the "Delete Message" button whereupon the system deletes the saved message; or (3) send the message by pressing the "Send" button. When the "Send" button is pressed the system displays a list with the patients contact— the relative network or address book—and the system prompts the patient to select the contacts which will receive the message. The patient selects one or more of the contacts and the system prompts the patient to press "Send". When the patient presses "Send" the system automatically sends the message to the inbox of the selected contacts in the system.

If the patient selects "Create New Text Message" the system shows the button "Send Message" and prompts the patient to enter the text message. After the message has been entered the system prompts the patient to press the "Send" button again. When the "Send" button is pressed the system displays a list with the patients contact—the relative network or address book—and the system prompts the patient to select the contacts which will receive the message. The patient selects one or more of the contacts and the system prompts the patient to press "Send". When the patient presses "Send" the system automatically sends the message to the inbox of the selected contacts in the system.

If in any case the message fails the system shows an alert notifying that the connection has some problems and asks that the relative try again in a moment and asks for confirmation from the patient.

If the patient selects PHOTO ALBUM the system shows some photos and the option "Previous Page" and "Next Page". If the patient selects "Previous Page" the system shows the previous group of photos. If the patient selects "Next Page" the system shows the next group of photos.

The patients photo album can be managed by relative (the legal guardian) or by the administrator. The user selects the MANAGE PATIENTS PICTURE ALBUM on the relative's menu options. The system shows a list with uploaded photos names and the options "Upload Photo" and "Delete Photo". If the user selects a photo from the list the system shows the selected photo. If the user selects "Upload Photo" the system shows a dialogue box allowing the user to select a photo from his computer's photo files, including the option of browsing on the user's computer to find the photo. The user selects the photo and presses "Accept". If the user selects "Delete Photo" then the system prompts the user to select the photos to be deleted and presses "Delete Photo" again to delete the photo.

Message Notification Management

It is important that the flow of message to the patients be monitored since they are notified in writing and choose to review messages at their leisure. Messages from relatives could sit unread in the system if the patient forgets they are there. Notification to the administrator operators is outlined above. The parameters for notifying relatives are entered by the administrator by choosing the New Message Notification option from main menu after logging on. If the user is an administrator with total access to all facilities the system prompts the user to select the patient's facility. The system then prompts the user to enter the patient's name whereupon the system displays the patients relative list. The system then prompts the user to select a relative from the list to edit his notification parameters. When a relative is selected the system the option to mark a relative to be notified and the number of days before notification. At this point the user may edit the parameters. The system then prompts the uses to press "Accept" to save the changes. If the user is only an operator at a specific facility the first step of selecting the facility is not required. Periodically, e.g., daily, the system searches marked as "Unread" in the "In Box" of II the patients. If an unread message is found for a patient the system searches all the users that must be notified when a message to that patient has not been read. The system then compares the message data (date and time) with the configurable "days before notify" value for those users and if that value is met or exceeded the system sends a notification to those users. The system marks the message as "notified" to avoid sending a notification alert for that message again.

If the relative is on-line and the Notification Tool is installed and running the Notification Tool searches for messages in his in box marked as "New" every ten minutes. The Notification Tool shows an alert message to the relative notifying that he has received one or more new messages from a patient showing the patient's name and the message subject. If the relative "clicks" over the Notification Tool tray icon the browser will open the relative's "in box" (RECEIVED MESSAGES).

Legal Guardian

As noted above one of the relatives is designated the LEGAL GUARDIAN of a patient. This relative has addition option on his main menu—MANAGE CONTACTS and MANAGE ACCOUNT. To manage the contacts on a patient's relative contact list (address book) the LEGAL GUARDIAN can suggest changes by choosing the MANAGE CONTACTS option. When this is chosen the system shows the patient's relatives list and the buttons "Request add New Contact" and "Request Remove Contact". If the user chooses the "Request add New Contact" option the system prompts the user to enter the new contact's first name, last name, user name, password, date of birth, gender, kinship and email. After the data is entered the system prompts the use to press the "Accept" button or suggest adding this relative. When the "Accept" button is pressed the system shows a message notifying that the suggestion is pending. If the user selects "Request Remove Contact" the system displays a list of the patient's contacts and prompts the user to select a contact from the list. After a contact has been selected the system prompts the user to press "Request Remove Contact" button to suggest removing the contact. After the "Request Remove Contact" button is pressed the system shows a message notifying that the suggestion is pending.

Also under the MANAGE CONTACTS option is the addition option Manage Status of Contacts which allows the LEGAL GUARDIAN to suggest that the contact who is the LEGAL GUARDIAN be added. When the user selects this option the system shows the patient's relative list and the button "Suggest Legal Guardian Status". The user selects a relative from the list and the system prompts to press the "Suggest Legal Guardian Status" button to suggest that this relative be a responsible Contact. After the "Suggest Legal Guardian Status" button is pressed the system shows a message notifying that the suggestion is pending.

If the LEGAL GUARDIAN chooses the MANAGE ACCOUNT option from the menu the system shows the patient's first name, last name and a list of all patient's relatives in the system. The system prompts the user to select a relative from the list and shows that relative's first name, last name, user name, password, date of birth, gender, kinship, and email. The system prompts the user to edit the relative's data and to press the "Accept" button to suggest the user data changes. The system shows a message notifying that the suggestion is pending.

The administrator or operator can manage the suggestion by choosing ADMINISTER CONTACT REQUESTS from the main menu. When chosen the system shows a list of the suggestions, specifying the kind of suggestion. The user selects a suggestion and the system displays the suggestion. Depending upon the type of suggestion and if agreeable, the user can invoke the Manage Relative Network to add, delete or edit relatives on a patient's list. The suggestion is automatically deleted from the system after it had been addressed.

The invention claimed is:

1. A method for communication between patients in a live-in facility and their relatives, comprising the steps of:
    (a) providing a host computer;
    (b) providing at least one terminal at said live-in facility having a data entry keyboard, mouse and screen, said terminal accessing said host computer;
    (c) providing a host operator who is designated as the administrator who can add, delete and edit the relatives and patients by assigning them user names and passwords;
    (d) identifying each of the patients, relatives and other operators by assigning a user name and password which is stored in the host computer;
    (e) associating the relatives of the individual patients with the patient and designating one relative of each patient as the legal guardian of that patient who may contact the administrator to suggest changes in the relatives who may access the patient;

(f) providing a secure web page accessible from terminals located at said live-in facility and computers operated by the relatives;
(g) providing a menu in said web page for choosing options to send or review messages sent to and from the relatives and patients;
(h) providing a message notification on said web page notifying the relatives that a message has been sent from a patient;
(i) providing a message notification on said web page that a patient has received a message from a relative; and
(j) providing an option in said menu to add, delete or edit the patient's and their relatives.

2. The method according to claim 1 wherein said menu on said terminal is addressed by touching the screen.

3. The method according to claim 1 further comprising providing hardware and software on said host computer to create, read and display text messages, video messages, audio messages and photographs.

4. The method according to claim 3 wherein the photographs are saved in a special separate file for and accessible by each patient.

5. The method according to claim 1 wherein each patient is notified in writing when they have received a message.

6. The method according to claim 5 wherein each message to each patient is marked when accessed.

7. The method according to claim 6 wherein selected the the legal guardian is notified when a message to a patient has been unaccessed for a specified period of time.

8. The method of claim 7 wherein the legal guardian is notified by a message on the web site when the legal guardian logs onto the website.

9. The method of claim 5 wherein the host computer prints out automatically prints out a notification when a patient receives a message and said notification is delivered to the patient.

* * * * *